(12) United States Patent
Oliver et al.

(10) Patent No.: US 12,105,109 B2
(45) Date of Patent: Oct. 1, 2024

(54) METHOD FOR ASSESSING DRY MATTER IN HORTICULTURAL PRODUCTS

(71) Applicant: The New Zealand Institute for Plant and Food Research Limited, Auckland (NZ)

(72) Inventors: Richard Jordan Oliver, Hamilton (NZ); Roderick Munro McDonald, Hamilton (NZ); Vincent Andrew McGlone, Hamilton (NZ); Richard John Seelye, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 1086 days.

(21) Appl. No.: 16/650,650

(22) PCT Filed: Sep. 26, 2018

(86) PCT No.: PCT/IB2018/057423
§ 371 (c)(1),
(2) Date: Mar. 25, 2020

(87) PCT Pub. No.: WO2019/064183
PCT Pub. Date: Apr. 4, 2019

(65) Prior Publication Data
US 2023/0243724 A1 Aug. 3, 2023

(30) Foreign Application Priority Data
Sep. 26, 2017 (NZ) ........................................ 735829

(51) Int. Cl.
*G01N 5/04* (2006.01)
*G01N 1/44* (2006.01)
(Continued)

(52) U.S. Cl.
CPC ............... *G01N 5/045* (2013.01); *G01N 1/44* (2013.01); *G01N 33/025* (2013.01); *G01N 2001/2866* (2013.01)

(58) Field of Classification Search
CPC ........ G01N 5/045; G01N 1/44; G01N 33/025; G01N 2001/2866
(Continued)

(56) References Cited

FOREIGN PATENT DOCUMENTS

| CN | 106289940 A | * | 1/2017 |
| WO | WO 2019/064183 | | 4/2019 |

OTHER PUBLICATIONS

International Search Report and Written Opinion, dated Nov. 27, 2018, corresponding to International Application No. PCT/IB2018/057423, from which the present application claims priority, 8 pp.
(Continued)

*Primary Examiner* — Robert R Raevis
(74) *Attorney, Agent, or Firm* — Leydig, Voit & Mayer, Ltd.

(57) ABSTRACT

The invention relates to a rapid method for estimating the dry matter content of a fruit or vegetable. The method comprises drying a sample of the fruit or vegetable on a support and measuring the dry matter content, wherein the whole method can be carried out in less than 2 hours. This compares to the industry standard method for assessing dry matter in horticultural products which typically takes 6-48 hours.

16 Claims, 10 Drawing Sheets

(51) Int. Cl.
*G01N 33/02* (2006.01)
*G01N 1/28* (2006.01)

(58) Field of Classification Search
USPC .............................................. 73/73; 426/231
See application file for complete search history.

(56) References Cited

OTHER PUBLICATIONS

Hickson (2006) "Quality assessment of avocados by means of dry matter content," Ministry of Agriculture and Rural Development Plant Protection and Inspection Services (PPIS) State of Israel, Presentation Jun. 2006 Slovak Republic, Mojmirovce (ITC), 44 pp.
Norell et al. (2016) "Measuring Potato Dry Matter Content on the Farm", University of Idaho Extension CIS 1219, Jan. 2016, [online], [retrieved from internet on Nov. 26, 2018] <URL:http://www.extension.uidaho.edu/publishing/pdf/CIS/CIS1219.pdf 3 pp.
Arpaia et al., "Development of a New Method for Measuring Minimum Maturity of Avocados", California Avocado Society 2001 Yearbook 85: 153-1781, Jan. 1, 2001.
"Determination of the moisture content for dried fruits", United Nations, Specialized Section on Standardization of Dry and Dried Produce (Fruit), 50$^{th}$ session, Jun. 2003, Geneva, Report of the Fiftieth Session, Oct. 6, 2003 (Oct. 6, 2003).
"Method for determination of dry matter and water content in fruit and vegetable products", National standards of the People's Republic of China, Standard No. GB 8858-1988, Jul. 1, 1988.
"Grain Dictionary", China Agriculture Press Printing House, Dec. 2009, 5 pages, 1st edition, China Material Press, No. 25 Yuetan North Street, Xicheng District, Beijing.
"Food Machinery and Equipment", Teaching materials for secondary specialized schools, 1999, 6 pages, No. 17532, China Light Industry Publishing House, , East Chang'an Street, Beijing, 100740, China.

\* cited by examiner (A)

(B)

METHOD FOR ASSESSING DRY MATTER IN HORTICULTURAL PRODUCTS

TECHNICAL FIELD

The invention relates to a method for estimating the dry matter content of a fruit or vegetable.

BACKGROUND

Dry matter of fruit and vegetables is an important indicator of taste quality.

For fruit such as kiwifruit and apples, dry matter (DM) includes accumulated sugars and starch, and is highly correlated with brix (sugar content) levels after ripening. Testing pre-harvest dry matter therefore provides a good indication of what the brix levels will be once the fruit has ripened. The higher the brix levels the more desirable the fruit. Thus a grower can make harvest timing decisions based on when the ideal dry matter content, and hence future brix level, is achieved. This helps ensure that the fruit will achieve a high taste standard. There is thus a high correlation between DM and consumer preference. Assessing DM beyond harvest (e.g. during fruit grading and sorting) is also a useful indicator of the quality of the fruit.

The industry standard method for assessing DM in fruit involves taking segment or thin slice of fruit and drying in an oven until weight loss is insignificant. For apples, the fruit segments or slices are dried for approximately 48 hours. For kiwifruit, slices are typically dried for 6 to 24 hours, depending on accuracy required. These lengthy periods represent a significant drawback to such methods for assessing DM.

Non-invasive methods for assessing DM have also been developed. For example, near-infra red (NIR) spectral systems are used during sorting and grading. However, the accuracy of such systems for assessing DM is limited at least in part by the NIR heads drifting and/or being affected by extraneous variations in fruit or vegetables condition (e.g. origin and/or maturity). Thus such systems need regular calibration using empirically derived DM data. As discussed above the current industry standard methods for assessing DM are lengthy which further adds to inconvenience in their use to calibrate NIR systems.

There thus exists a need for more convenient, and/or quicker methods for estimating DM in fruit and vegetables, for use in assessing fruit/vegetable quality as discussed, and/or for use in calibrating instruments for assessing DM.

It is therefore an object of this invention to go some way towards achieving one or more of these desiderata or at least to offer the public a useful choice.

Any discussion of documents, acts, materials, devices, articles or the like which has been included in the present specification is solely for the purposes of providing a context for the present invention. It is not to be taken as an admission that any or all of these matters form part of the prior art base or were common general knowledge in the field relevant to the present invention as it existed before the priority date.

SUMMARY OF THE INVENTION

In one aspect, the invention provides a method for estimating the dry matter content of a fruit or vegetable, the method comprising the steps a) providing material from the fruit or vegetable,
b) homogenising the material,
c) applying a portion of the material to a support,
d) weighing the support and homogenised material,
e) drying the homogenised material,
f) weighing the support and dried homogenised material, and
g) calculating dry matter content of the homogenised material based on the difference between the weight of the support and homogenised material and the weight of the support and dried homogenised material, wherein the dry matter content of the homogenised material provides the estimate of the dry matter content of the fruit or vegetable.

In one embodiment the material is from the part of the fruit or vegetable that is consumed.

In one embodiment the fruit or vegetable is a fruit or vegetable for which dry matter is used as indicator of quality, preferably the fruit or vegetable is selected from the group consisting of kiwifruit, apples, pears, mangoes, melons, bananas, avocadoes, tomatoes, onions, potatoes, sweet potatoes and kumara, preferably kiwifruit, mangoes and avocado, more preferably kiwifruit.

In one embodiment the material is from the outer pericarp of a fruit.

In one embodiment the amount of any non-outer pericarp tissue amounts to less than 20%, more preferably less than 10%, more preferably less than 5%, more preferably less than 2%, more preferably less than 1% w/w of the material.

In one embodiment the material is composed entirely of outer pericarp tissue.

In one embodiment homogenising breaks open cells in the material.

In one embodiment homogenising the material comprises forcing the material through a small aperture.

In one embodiment homogenising the material comprises crushing the material.

In one embodiment the aperture is no more than 5 mm in diameter, more preferably no more than 3 mm, more preferably no more than 1 mm, more preferably no more than 0.7 mm, more preferably no more than 0.5 mm in diameter.

In one embodiment the aperture is about 0.4 mm in diameter, preferably the aperture is 0.4 mm in diameter.

In one embodiment the material is forced through the aperture under pressure.

The method, wherein the force is sufficient to break open cells in the material.

In one embodiment a force in the range 3 to 100 kN is applied.

In one embodiment the material is forced through the aperture at a pressure in the range 50 to 1200 psi.

In one embodiment the portion of homogenised material weighs no more than 10 g, preferably no more than 5 g, more preferably no more than 3 g, more preferably no more than 1 g, more preferably no more than 0.7 g, more preferably no more than 0.5 g, more preferably no more than 0.3 g, more preferably no more than 0.1 g.

In one embodiment the homogenised material weighs about 0.3 g or about 0.5 g, preferably the homogenised material weighs 0.3 g or 0.5 g.

In one embodiment the support is or comprises at least one piece of absorbent material.

In one embodiment the support is or comprises at least two pieces of absorbent material.

In one embodiment the material is homogenised on a support comprising at least two pieces of absorbent material.

In one embodiment the absorbent material is or comprises paper.

In one embodiment the paper is or comprises cellulosic paper, or is or comprises glass fibre paper.

In one embodiment the absorbent material is or comprises polypropylene or polyethylene, preferably polypropylene.

In one embodiment the material is dispersed on the support to form a thin film and/or to increase the surface area of the material.

In one embodiment the homogenised material is dried by the application of at least one of:
heat, and
air flow or turbulence.

In one embodiment the homogenised material is subjected to a temperature of at least 20° C., preferably the homogenised material is subjected to a temperature of at least 50, more preferably at least 100, more preferably at least 110, more preferably at least 120, more preferably at least 130, more preferably at least 140, more preferably at least 150° C.

In one embodiment the homogenised material is subjected to a temperature in the range 50 to 250° C., preferably the homogenised material is subjected to a temperature in the range 100 to 200, more preferably in the range 110 to 160, more preferably in the range 120 to 150° C.

In one embodiment the homogenised material is subjected to a temperature of about 150° C., preferably wherein the homogenised material is subjected to a temperature of 150° C.

In one embodiment the homogenised material is subjected to a temperature of about 120° C., preferably wherein the homogenised material is subjected to a temperature of 120° C.

In one embodiment the heat and/or air flow is applied to both sides of the support.

In another aspect, the invention provides a method for estimating the dry matter content of a fruit or vegetable, the method comprising the steps
a) providing material from the fruit or vegetable,
b) homogenising the material on a support,
c) weighing the support and homogenised material,
d) drying the homogenised material,
e) weighing the support and dried homogenised material, and
f) calculating dry matter content of the homogenised material based on the difference between the weight of the support and homogenised material and the weight of the support and dried homogenised material,
wherein the dry matter content of the homogenised material provides the estimate of the dry matter content of the fruit or vegetable.

In one embodiment the material is from the part of the fruit or vegetable that is consumed.

In one embodiment the fruit or vegetable is a fruit or vegetable for which dry matter is used as indicator of quality, preferably the fruit or vegetable is selected from the group consisting of kiwifruit, apples, pears, mangoes, melons, bananas, avocadoes, tomatoes, onions, potatoes, sweet potatoes and kumara, preferably kiwifruit, mangoes and avocado, more preferably kiwifruit.

In one embodiment the material is from the outer pericarp of a fruit.

In one embodiment the amount of any non-outer pericarp tissue amounts to less than 20%, more preferably less than 10%, more preferably less than 5%, more preferably less than 2%, more preferably less than 1% w/w of the material.

In one embodiment the material is composed entirely of outer pericarp tissue.

In one embodiment homogenising breaks open cells in the material.

In one embodiment homogenising the material comprises forcing the material through a small aperture.

In one embodiment homogenising the material comprises crushing the material.

In one embodiment the aperture is no more than 5 mm in diameter, more preferably no more than 3 mm, more preferably no more than 1 mm, more preferably no more than 0.7 mm, more preferably no more than 0.5 mm in diameter.

In one embodiment the aperture is about 0.4 mm in diameter, preferably the aperture is 0.4 mm in diameter.

In one embodiment the material is forced through the aperture under pressure.

The method, wherein the force is sufficient to break open cells in the material.

In one embodiment a force in the range 3 to 100 kN is applied.

In one embodiment the material is forced through the aperture at a pressure in the range 50 to 1200 psi.

In one embodiment the portion of homogenised material weighs no more than 10 g, preferably no more than 5 g, more preferably no more than 3 g, more preferably no more than 1 g, more preferably no more than 0.7 g, more preferably no more than 0.5 g, more preferably no more than 0.3 g, more preferably no more than 0.1 g.

In one embodiment the homogenised material weighs about 0.3 g or about 0.5 g, preferably the homogenised material weighs 0.3 g or 0.5 g.

In one embodiment the support is or comprises at least one piece of absorbent material.

In one embodiment the support is or comprises at least two pieces of absorbent material.

In one embodiment the material is homogenised on a support comprising at least two pieces of absorbent material.

In one embodiment the absorbent material is or comprises paper.

In one embodiment the paper is or comprises cellulosic paper, or is or comprises glass fibre paper.

In one embodiment the absorbent material is or comprises polypropylene or polyethylene, preferably polypropylene.

In one embodiment the material is dispersed on the support to form a thin film and/or to increase the surface area of the material.

In one embodiment the homogenised material is dried by the application of at least one of:
heat, and
air flow or turbulence.

In one embodiment the homogenised material is subjected to a temperature of at least 20° C., preferably the homogenised material is subjected to a temperature of at least 50, more preferably at least 100, more preferably at least 110, more preferably at least 120, more preferably at least 130, more preferably at least 140, more preferably at least 150° C.

In one embodiment the homogenised material is subjected to a temperature in the range 50 to 250° C., preferably the homogenised material is subjected to a temperature in the range 100 to 200, more preferably in the range 110 to 160, more preferably in the range 120 to 150° C.

In one embodiment the homogenised material is subjected to a temperature of about 150° C., preferably wherein the homogenised material is subjected to a temperature of 150° C.

In one embodiment the homogenised material is subjected to a temperature of about 120° C., preferably wherein the homogenised material is subjected to a temperature of 120° C.

In one embodiment the heat and/or air flow is applied to both sides of the support.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Although the present invention is broadly as defined above, those persons skilled in the art will appreciate that the invention is not limited thereto and that the invention also includes embodiments of which the following description gives examples.

Disclosure of the Invention

The invention provides a novel rapid method for estimating the dry matter content of a fruit or vegetable.

The inventors have surprisingly shown that the novel method can produce equivalent results to the industry standard method but in a very small fraction of the time. Whereas the industry standard method takes 6 to 48 hours, the novel method of the invention can be completed in less than 10 mins. The new method therefore clearly provides a very significant advantage to the horticultural industry.

Method

In the first aspect the invention provides a method for estimating the dry matter content of a fruit or vegetable, the method comprising the steps a) providing material from the fruit or vegetable,
b) homogenising the material,
c) applying a portion of the material to a support,
d) weighing the support and homogenised material,
e) drying the homogenised material,
f) weighing the support and dried homogenised material, and
g) calculating dry matter content of the homogenised material based on the difference between the weight of the support and homogenised material and the weight of the support and dried homogenised material, wherein the dry matter content of the homogenised material provides the estimate of the dry matter content of the fruit or vegetable.

Those skilled in the art will understand that order of the steps above may be altered without departing from the scope of the invention. For example, the material may be homogenised on the support as in the alternative embodiment described below.

Material

In one embodiment the material is from the part of the fruit or vegetable that is consumed.

In one embodiment the material is from a fruit.

In one embodiment the material is from the outer pericarp of a fruit.

In a preferred embodiment the material is from the outer pericarp of a kiwifruit.

Although not preferred, the material may include a proportion of non-outer pericarp tissue (e.g. skin, inner pericarp, seed, etc.). Preferably any non-outer pericarp tissue amounts to less than 20%, more preferably less than 10%, more preferably less than 5%, more preferably less than 2%, more preferably less than 1% w/w of the material.

In a preferred embodiment the material is composed entirely of outer pericarp tissue.

Homogenising

In one embodiment the homogenising breaks open cells in the material. In a further embodiment breaking open cells exposes cellular water content. In a further embodiment exposing cellular water content facilitates more rapid drying. In some embodiments, the term homogenising can be considered synonymous with cell lysis and/or cell disruption. In other embodiments the material is homogenised in such a way to aid the subsampling process. For example, by producing a gel that reduces the separation of the sampled material. In one embodiment homogenising means that all fractions of a sample are equal in composition.

Any known method for homogenising plant material may be used. For example a blender-type homogeniser may be used. A blender-type homogeniser may be effectively used in combination with freezing and thawing of the material.

In one embodiment the material may be homogenised by being crushed in a press such as an arbor press or a hydraulic press. A hydraulic press may be preferred for crushing hard fruit or vegetables while an arbor press may be preferred for soft fruit or vegetables.

In one embodiment the material is homogenised by being forced through a small aperture.

In a further embodiment the material is forced through the aperture under pressure.

In a further embodiment the aperture is no more than 5 mm in diameter. Preferably the aperture is no more than 4 mm, more preferably no more than 3 mm, more preferably no more than 2 mm, more preferably no more than 1 mm, more preferably no more than 0.9 mm, more preferably no more than 0.8 mm, more preferably no more than 0.7 mm, more preferably no more than 0.6 mm, more preferably no more than 0.5 mm in diameter.

Preferably the aperture is about 0.4 mm in diameter.

Preferably the aperture is 0.4 mm in diameter.

In one embodiment the material is forced through the aperture by a pneumatic ram operating at a pressure in the range 50 to 1000 psi. Those skilled in the art will understand the more pressure (at the higher end of the range) will be required when using less ripe, or firmer, fruit or vegetables and that less pressure (at the lower end of the range) will be required when using riper, or softer fruit or vegetables.

For example, for softer fruit or vegetables at harvest, the pneumatic ram operates at a pressure in the range of 80 to 160, more preferably 90 to 150, more preferably 100 to 140, more preferably 110 to 130. Preferably for softer fruit or vegetables at harvest, the pneumatic ram operates at a pressure of about 120 psi. More preferably for softer fruit or vegetables at harvest, the pneumatic ram operates at a pressure of 120 psi.

Likewise, for example, for firmer fruit or vegetables, the pneumatic ram operates at a pressure in the range of 500 to 1200, more preferably 600 to 1100, more preferably 700 to 1000, more preferably 800 to 900 psi.

Portion of Homogenised Material

In one embodiment the portion of homogenised material weighs no more than 10 g. Preferably the portion of homogenised material weighs no more than 9 g, more preferably no more than 8 g, more preferably no more than 7 g, more preferably no more than 6 g, more preferably no more than 5 g, more preferably no more than 4 g, more preferably no more than 3 g, more preferably no more than 2 g, more preferably no more than 1 g, more preferably no more than 0.9 g, more preferably no more than 0.8 g, more preferably no more than 0.7 g, more preferably no more than 0.6 g, more preferably no more than 0.5 g, more preferably no more than 0.4 g, more preferably no more than 0.3 g, more preferably no more than 0.2 g, more preferably no more than 0.1 g.

Preferably the homogenised material weighs about 0.3 g or 0.5 g. Preferably the homogenised material weighs 0.3 g or 0.5 g.

Support

In one embodiment the support is or comprises at least one piece of absorbent material. In this context, an absorbent material includes a material with a matrix that allows for the fruit or vegetable material to be suspended either in spaces between the fibres or in the matrix of the absorbent material by surface tension and capillary effects.

In a further embodiment the support is or comprises at least two pieces of absorbent material.

Preferably the moisture content of the absorbent material is known. In one embodiment the moisture content is known because the absorbent material has been pre-dried, or stored at a known humidity and temperature.

In one embodiment the absorbent material is or comprises paper.

In one embodiment the paper is or comprises cellulosic paper. Preferably the moisture content of the cellulosic paper is known as discussed above.

Preferably the absorbent material is or comprises glass fibre paper.

An advantage of glass fibre paper is to avoid the need to compensate for the presence of water in the support.

By way of example suitable glass fibre paper is Whatman Glass Microfibre Filters GF/A, 70 mm diameter (Cat No 1820-070).

Preferably the absorbent material is or comprises a plastic polymer, for example polytetrafluoroethylene, polyethylene, polypropylene, acetate, tri-acetate, nylon, terylene, polyacrylonitrile or polyvinyl alcohol.

By way of example suitable polypropylene is 60 gsm spun bonded polypropylene such as that obtained from IndTex (Auckland, New Zealand).

Polypropylene can also be provided in a hydrophilic formulation, which might help reduce loss of sample to the spreading or crushing surfaces.

An advantage of polypropylene and polyethylene is that they have zero moisture content.

Spreading the Material on the Support

In one embodiment the material is dispersed to form a thin film. In a further embodiment the material is dispersed to increase the surface area of the material. In a further embodiment the material is dispersed to form a film and increase the surface area of the material.

In a preferred embodiment the material is dispersed between a support comprising at least two pieces of absorbent material. It will be understood that the two pieces can be formed by folding a single piece.

In a preferred embodiment the material is dispersed, under pressure, between a support comprising the at least two pieces of absorbent material.

Alternative Embodiment with Homogenisation on the Support

In an alternative embodiment the material is homogenised on the support. The alternative method is based on the method described above, but is designed to cope with potential situations in which a homogeneous and representative pulp sample is not required, might not be reliably obtainable, or cannot be subsampled with confidence. For example when the fruit or vegetable is too hard to homogenise or too soft to peel; or if machine stresses or complex cleaning procedures led to unreliability; or if the fruit or vegetable sample is required to include skin or seeds, e.g. a cross-sectional slice of fruit.

In a preferred form of this alternative embodiment the material is homogenised on a support comprising at least two pieces of absorbent material.

In one embodiment the absorbent material is or comprises cellulosic paper or glass fibre paper.

Preferably the absorbent material is or comprises a plastic polymer, for example polytetrafluoroethylene, polyethylene, polypropylene, acetate, tri-acetate, nylon, terylene, polyacrylonitrile or polyvinyl alcohol.

By way of example suitable polypropylene is 60 gsm spun bonded polypropylene such as that obtained from IndTex (Auckland, New Zealand).

Polypropylene can also be provided in a hydrophilic formulation, which might help reduce loss of sample to the spreading or crushing surfaces.

An advantage of polypropylene and polyethylene is that they have zero moisture content.

In a preferred embodiment the force is sufficient to break open cells in the material.

In one embodiment a force in the range 3 to 100 kN is applied.

Those skilled in the art will understand the more force (at the higher end of the range) will be required when using less ripe, or firmer, fruit or vegetables and that less force will be required when using riper, or softer fruit or vegetables.

For example, for softer fruit or vegetables at harvest, a force in the range of 3 to 11, more preferably 4 to 9, more preferably 5 to 8, more preferably 6 to 7 kN is applied. Preferably for softer fruit or vegetables at harvest, a force about 6.5 kN is applied. More preferably for softer fruit or vegetables at harvest, a force 6.5 kN is applied.

Likewise, for example, for firmer fruit or vegetables, a force in the range of 20 to 100, more preferably 30 to 90, more preferably 40 to 80 kN is applied.

In one embodiment the force is applied through use of a press. In a further embodiment the press is an arbor press. In a further embodiment the press is a hydraulic press. A hydraulic press may be preferred for crushing hard fruit or vegetables while an arbor press may be preferred for soft fruit or vegetables.

In this embodiment, the material to be homogenised on the support preferably weighs no more than 10 g. Preferably the material weighs no more than 9 g, more preferably no more than 8 g, more preferably no more than 7 g, more preferably no more than 6 g, more preferably no more than 5, more preferably no more than 4 g, more preferably no more than 3 g, more preferably no more than 2 g, more preferably no more than 1 g, more preferably no more than 0.9 g, more preferably no more than 0.8 g, more preferably no more than 0.7 g, more preferably no more than 0.6 g, more preferably no more than 0.5 g, more preferably no more than 0.4 g, more preferably no more than 0.3 g, more preferably no more than 0.2 g, more preferably no more than 0.1 g.

Weighing

Preferably the material is weighed in grams (g) to at least 1 decimal place. Preferably the material is weighed in grams (g) to at least 2 decimal places, more preferably at least 3, more preferably at least 4, more preferably at least 5 decimal places.

The material may also be weighed in other units, preferably to equivalent precision.

Any suitable balance may be used for the weighing.

In one embodiment the balance weighs in grams (g) to at least 1 decimal place. Preferably the balance weighs in grams (g) to at least 2 decimal places, more preferably at least 3, more preferably at least 4, more preferably at least 5 decimal places.

Balances that use other units, with equivalent precision may of course, also be used.

Drying

In one embodiment the homogenised material is dried by the application of at least one of:

a) heat, and b) air flow or turbulence.

With respect to heat, in one embodiment the homogenised material is subjected to a temperature of at least 20° C. Preferably the homogenised material is subjected to a temperature of at least 30, more preferably at least 40, more preferably at least 50, more preferably at least 60, more preferably at least 70, more preferably at least 80, more preferably at least 90, more preferably at least 100, more preferably at least 110, more preferably at least 120, more preferably at least 130, more preferably at least 140, more preferably at least 150° C.

In one embodiment the homogenised material is subjected to a temperature in the range 50 to 250° C. Preferably the homogenised material is subjected to a temperature in the range 60 to 240, more preferably in the range 70 to 230, more preferably in the range 80 to 220, more preferably in the range 90 to 210, more preferably in the range 100 to 200, more preferably in the range 110 to 190, more preferably in the range 120 to 180° C., more preferably in the range 130 to 170° C., more preferably in the range 140 to 160° C., more preferably in the range 145 to 155° C.

Preferably the homogenised material is subjected to a temperature of about 120° C. or 150° C.

Preferably the homogenised material is subjected to a temperature of 120° C. or 150° C.

Preferably the homogenised material is subjected to turbulent air at the temperature, or within the temperature range, described above.

In one embodiment air flows is directed toward, or over, the homogenised material.

In one embodiment the air flow is at a rate of at least 10 litres per minute (L/min). Preferably, the air flow is at a rate of at least 50, more preferably at least 100, more preferably at least 200, more preferably at least 300, more preferably at least 400, more preferably at least 500, more preferably at least 600, more preferably at least 700, more preferably at least 800, more preferably at least 900, more preferably at least 1000 L/min.

In a preferred embodiment the air is at the temperature, or within the temperature range described above.

In one embodiment the homogenised material is dried using one or more hot air gun(s). In one embodiment the hot air is directed at the homogenised material. In a preferred embodiment the homogenised material is sandwiched between two pieces of absorbent material and two hot air guns are used to direct hot air at both sides of the support. A suitable hot air gun, by way of example, is the BOSCH-PHG 630 DCE hot air gun.

In one embodiment the homogenised material is dried until substantially all the liquid content is removed. In a further embodiment the homogenised material is dried until all the liquid content is removed. In a further embodiment the homogenised material is dried until its weight no longer decreases. Preferably the liquid is water.

Preferably substantially no solids are removed during drying of the homogenised material. More preferably, no solids are removed during drying of the homogenised material.

Preferably there are no chemical or oxidation reactions during the drying process that cause loss or gain of solid matter at a magnitude that would make a significant difference to the DM calculation.

In one embodiment the homogenised material is dried for no more than 120 minutes. Preferably the homogenised material is dried for no more than 110, more preferably no more than 100, more preferably no more than 90, more preferably no more than 80, more preferably no more than 70, more preferably no more than 60, more preferably no more than 50, more preferably no more than 40, more preferably no more than 30, more preferably no more than 20, more preferably no more than 10, more preferably no more than 9, more preferably no more than 8, more preferably no more than 7, more preferably no more than 6, more preferably no more than 5, more preferably no more than 4, more preferably no more than 3, more preferably no more than 2 minutes, more preferably no more than 1 minute.

Calculating Dry Matter Content

Dry matter content of the fruit or vegetable may be calculated by dividing the weight of the dried material by the weight of the non-dried material.

Percentage dry matter may be calculated by dividing the weight of the dried material by the weight of the non-dried material, and multiplying by 100.

Timing for the Whole Method

In one embodiment the whole method can be completed in 120 minutes. Preferably the whole method can be completed in 110, more preferably in 100, more preferably in 90, more preferably in 80, more preferably in 70, more preferably in 60, more preferably in 50, more preferably in 40, more preferably in 30, more preferably in 20, more preferably in 19, more preferably in 18, more preferably in 17, more preferably in 16, more preferably in 15, more preferably in 14, more preferably in 13, more preferably in 12, more preferably in 11, more preferably in 10, more preferably in 9, more preferably in 8, more preferably in 7, more preferably in 6, more preferably in 5 minutes, more preferably in 4 minutes, more preferably in 3 minutes, more preferably in 2 minutes.

Fruit

The fruit may be any fruit. Preferably the fruit is a fruit for which dry matter is used as indicator of fruit quality.

For example the fruit may be selected from kiwifruit, apples, pears, mangoes, melons, and bananas.

Preferred fruit include kiwifruit and mangoes.

A particularly preferred fruit is kiwifruit.

Vegetable

The vegetable may be any vegetable. Preferably the vegetable is a vegetable for which dry matter is used as indicator of vegetable quality.

For example the vegetable may be selected from avocadoes, tomatoes, onions, potatoes, sweet potatoes and kumara.

A preferred vegetable is an avocado.

Applications for the Method

The method of the invention clearly offers significant advantage over the widely used industry standard methods for assessing dry matter in fruit and vegetable samples, particularly in terms of the rapidity of the method for generating reproducible, accurate, dry matter content estimates for fruit and vegetables in a very much shorter time than the industry standard methods.

As demonstrated in the Example below the method of the invention, can therefore be conveniently used in place of the lengthy industry standard methods.

Data for dry matter content conveniently and rapidly produced by the method of the invention, can also be conveniently used to calibrate devices for assessing dry matter, including non-invasive devices such as near-infra red (NIR based) devices that are very prone to drift, and require regular calibration.

BRIEF DESCRIPTION OF THE FIGURES

The present invention will be better understood with reference to the accompanying non-limiting drawings in which.

EXAMPLES

The invention will now be illustrated with reference to the following non-limiting examples.

It is not the intention to limit the scope of the invention to the below mentioned examples only. As would be appreciated by a skilled person in the art, many variations are possible without departing from the scope of the invention.

Example 1

The method of the invention is exemplified below using kiwifruit. Those skilled in the art will appreciate that the method can also be performed using other fruit and vegetables.

Summary

The Gold3 kiwifruit cultivar (*Actinidia chinensis* var. *chinensis* 'Zesy002') was evaluated for destructive analysis of dry-matter contents.

The rapid dry-matter measurement method of the invention was compared to the industry standard reference dry-matter measurement (involving 24 hours of drying) to assure that the rapid method of the invention is an accurate and feasible alternative to the industry standard methods.

The aim was for the rapid dry matter method of the invention to produce dry-matter results which are consistent (linear in relationship) and reproducible with a desirable standard deviation less than 0.2% FW, against equivalent oven dried pulp samples, and less than 0.5% FW against the oven dried slice samples.

Isolation of Outer Pericarp Material

Kiwifruit outer pericarp was isolated for use in the method of the invention and in the industry standard oven dry matter (Oven DM) method involving 24 hours of drying.

The skin and seeds were dissected out using a knife and peeler on a chopping board, leaving as much of the outer pericarp as possible.

The outer pericarp was then cut up into smaller pieces and mixed on the chopping board to assure a homogenous sample.

Homogenisation of the Outer Pericarp—to Produce a Pulp

Figure 1:
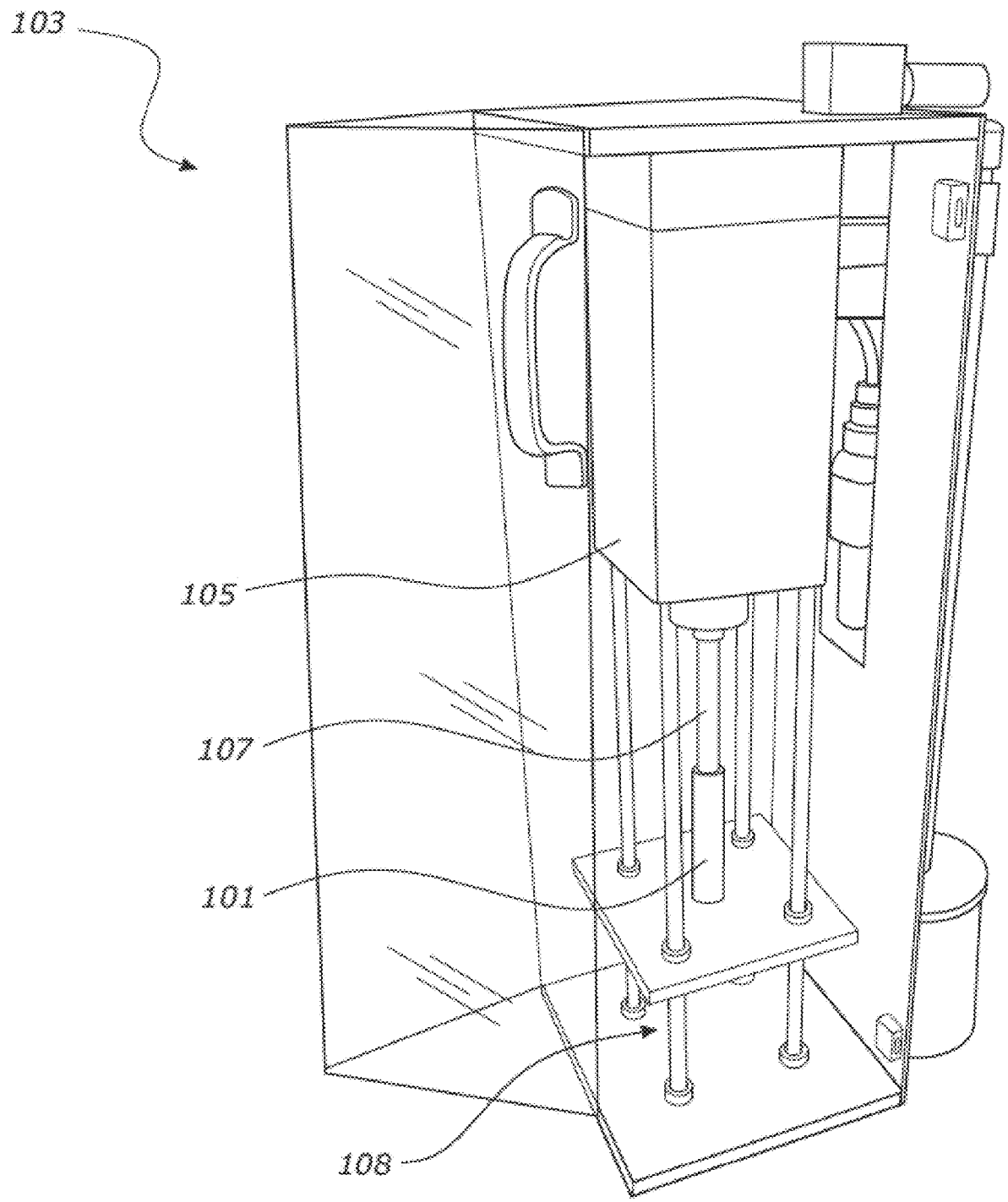
FIG. 1 shows a homogeniser component (plate homogeniser) used for homogenising the material to form a pulp.

A sample of outer pericarp (about 20 g) was placed into a small cylinder 101, of internal diameter 16.00 mm, open at the top end but closed at the bottom with a plate containing a 0.4 mm diameter hole in the middle. This cylinder was placed into the plate homogenizer 103 (termed the 'pulper'). The plate homogenizer 103 was created in the applicant's workshop according to the requirements of the experiment (FIG. 1).

High force is provided by a 125 mm diameter pneumatic ram 105 was used to push a 16.00 mm diameter piston 107 down into the cylinder, forcing the outer pericarp tissue through the 0.4 mm diameter hole. The piston with an "O" ring (111N70) secured 2 mm from the front end, preventing material escaping back up the piston, between the piston and the cylinder. The shear forces created in driving the material through the hole are sufficient to cause complete cellular rupture of the kiwifruit tissue and provide a homogenous pulp. The pulp can be received in a receptacle positioned at a location 108 below the cylinder.

Kiwifruit Slice Preparation

For the standard reference dry-matter method (Oven Slice DM) an equatorial 3 mm slice of the kiwifruit was prepared with the skin and seeds still intact.

Industry Standard (Conventional) Dry-Matter Method for Reference

For comparison, and to determine the accuracy of the rapid dry-matter method of the invention, industry standard methods for calculating dry matter were performed.

Both kiwifruit pulp (homogenised material) and kiwifruit slices were used. Generally 1-2 equatorial slices were used per kiwifruit and at least 3 kiwifruit pulp dishes were used per kiwifruit for the reference.

Both the kiwifruit pulp and slice were used in the same method and is as follows:
1. Using a maker pen, record the date, fruit sample number and pulp/slice number (if using more than one) on petri dishes.
2. Weigh the petri dishes on a scale with at least 3 decimal points and record the weights ('dish wt') in the excel spread sheet.
3. Place the pulp (about 4 g)/slice onto the petri dishes then record the weight ('dish+pulp wt') again.
4. Place the petri dishes with kiwifruit sample in an oven set at 65° C. for 24 hours. Make sure to record the time in which the petri dishes were placed in the oven.
5. Once 24 hours have passed, remove the petri dishes from the oven, allow them to cool for a few minutes, then record the weight ('dry wt').

The dry matter content is calculated by using the following formula;

$$DM = \frac{100((\text{dish} + \text{dry wt}) - \text{dish wt})}{((\text{dish} + \text{wet wt}) - \text{dish wt})}$$

Rapid Dry-Matter Method of the Invention

Figure 2:
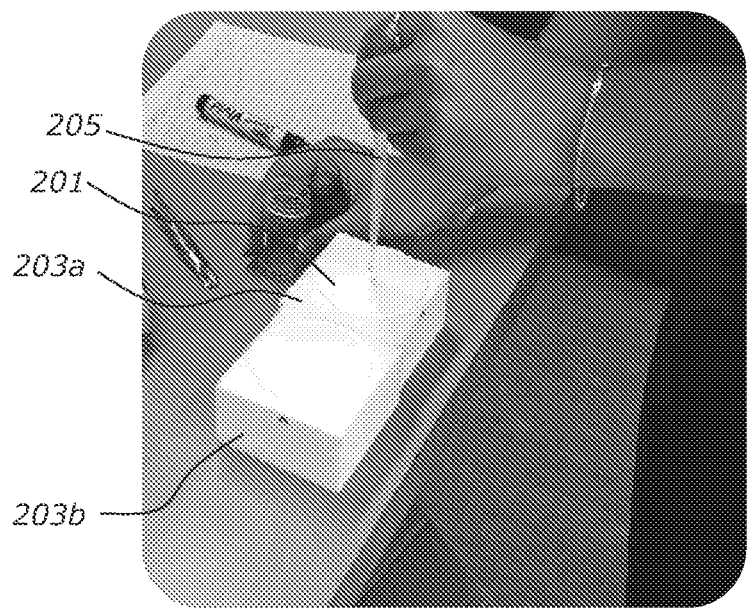
FIG. 2A shows application of the homogenised material (pulp) to a support comprising two circular pieces of glass fibre paper.
FIG. 2B shows the material about to be spread on the support by application of moderate force between two Teflon blocks.
Figure 2:
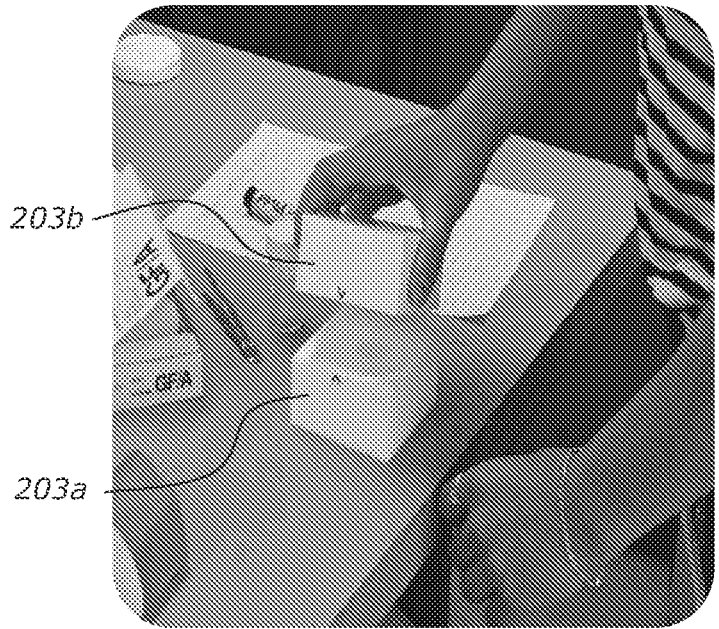
Figure 3:
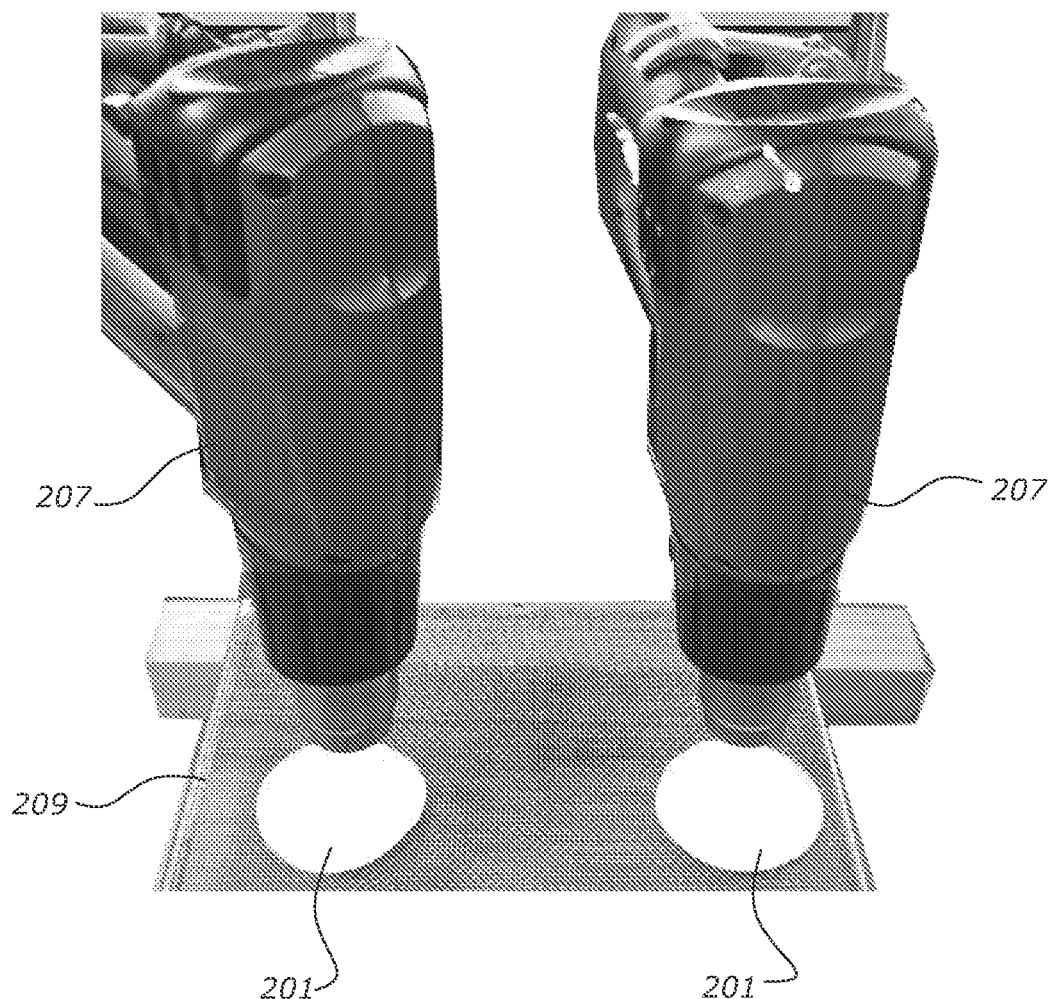
FIG. 3 shows drying components (heat guns) positioned to dry the homogenised material on support comprising two circular pieces of glass fibre paper.
Figure 4:
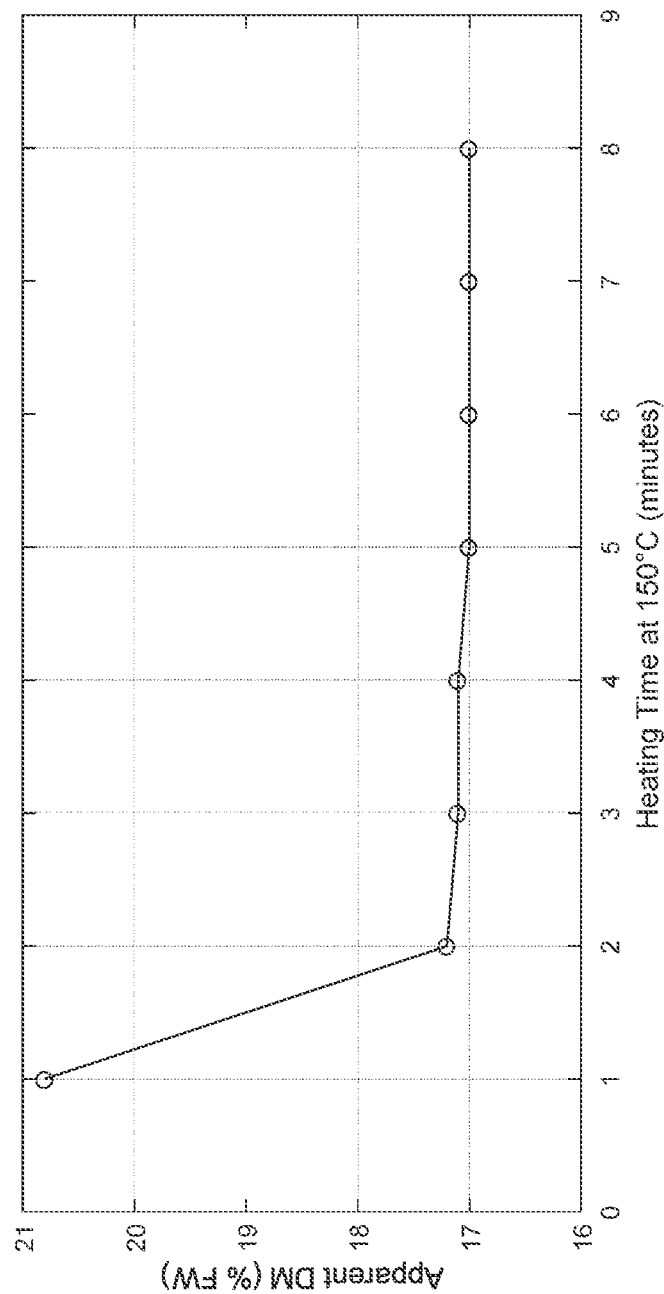
FIG. 4 shows the change in apparent dry matter DM with heating time.

The method for the rapid dry-matter experiment using glass fibre paper 201 is as below:
1. Place a small, closed container (e.g., a plastic petri dish with lid) on the mass balance and zero the balance. This small, closed plastic container is used to contain the GF paper+pulp to prevent the pulp sample changing weight during the weighing process, which may take some seconds. Avoiding exposure to the environment during the weighing process helps to stabilise the weight of the pulp.
2. Weigh both pieces of glass fibre (GF; Whatman Glass Microfibre Filters GF/A, 70 mm diameter, Cat No 1820-070) paper using a five decimal point weigh scale and record the weight. Use flat nose tweezers to handle the delicate glass fibre paper.
3. Place the GF paper 201 on a small Teflon block 203a and remove the top paper.
4. Place about 0.5 g (variation 0.2-1.2 g) of kiwifruit pulp on the GF paper resting on the Teflon block using a small plastic pipette 205 (FIG. 2A) and place the previously removed GF paper 201 on top of the pulp sample. Place another block 203b on top and press firmly together without any rotation (FIG. 2B).
5. Switch on the BOSCH-PHG 630 DCE, or similar, hot air gun 207 to setting 3 at 150° C. The hot air gun 207 will be secure in a retort stand set 4 cm away from the mesh 209 (FIG. 3). It is important to switch on the hot air gun prior 207 to use as it takes time for the hot air gun to heat up to the required temperature.
6. Place the GF paper+pulp (sandwich) sample inside the small plastic container, on the weight scale, and record the weight.
7. Carefully pull apart the two GF papers 201 and be careful to assure there are no blobs or ridges of pulp. If there is, rub/rotate the two GF papers together to assure even distribution.
8. Place each GF paper 201 on the mesh 209, one GF paper under one gun, pulp side up.
9. Heat both pieces of GF papers using the BOSCH-PHG 630 DCE, or similar, at setting 3, for 2 minutes at 150° C. (FIG. 3).
10. Place both pieces of paper 201 together again and place inside the small plastic container on the weight scales. Record the weight. The final weight reading needs to happen quickly as the dried pulp will start to absorb moisture from the air which will affect the weight, hence the dry matter content.

Results

Figure 5:
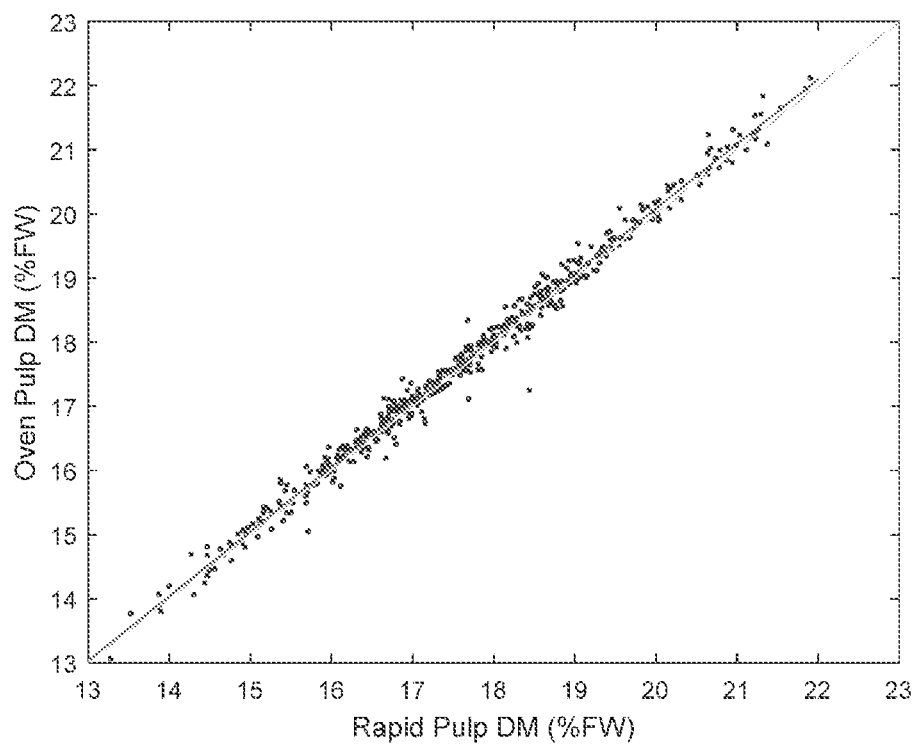
FIG. 5 shows the relationship between dry matter (DM) as estimated with the rapid pulp dry matter method of the invention, and dry matter (DM) as calculated with an industry standard Oven Pulp DM method.
Figure 6:
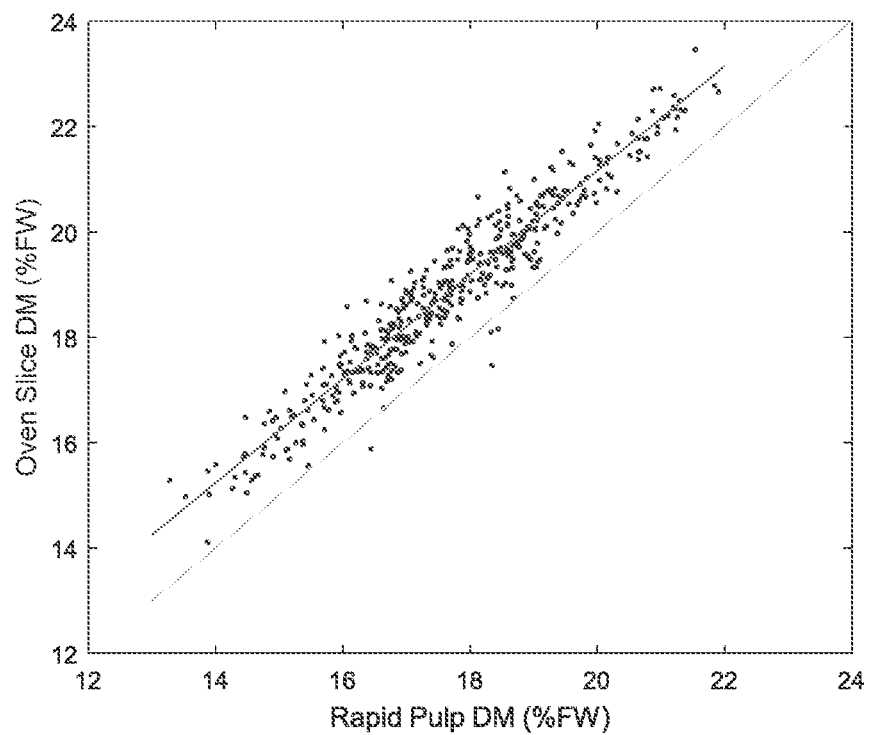
FIG. 6 shows the relationship between dry matter (DM) as estimated with the rapid pulp dry matter method of the invention, and dry matter (DM) as calculated with an industry standard Oven Slice DM method.

Two minutes heating by the hot air gun system 207 was sufficient to take the pulp sample very close to an asymptotic weight (FIG. 5). The calculated Rapid Pulp DM values were highly correlated with both the values obtained using the Oven Pulp DM method (FIG. 5) and the Oven Slice DM method (FIG. 6).

The correlation with the Oven Pulp DM values was very high ($R2=0.99$), linear with slope close to 1, a very small average bias ($-0.07\%$ FW) and a low root mean square error (rmse)=$0.19\%$ FW. This proves the Rapid Pulp DM method is very accurate for measuring expected Oven Pulp DM values.

The correlation with the Oven Slice DM values was also high ($R2=0.92$) and the relationship was again very linear with slope close to 1. However the average bias was large ($-1.19\%$ FW) and the root mean square error (rmse)=$0.48\%$ FW. The reason there is bias is largely because the outer pericarp, from which the pulp is made, is not representative of the same tissue used with the Oven Slice DM method, which includes the inner pericarp, containing seeds, and the central white core of the fruit. Those two regions have different DM, slightly higher than the outer pericarp. As can be observed, the bias difference is just a fixed offset for the fruit examined here but, because fruit structure is largely genetic, the bias is probably also a constant for a cultivar. The root mean square error (rmse) is probably large due to matters like random fluctuations in seed count, in the inner pericarp tissue of the slice sample.

Figure 7A:
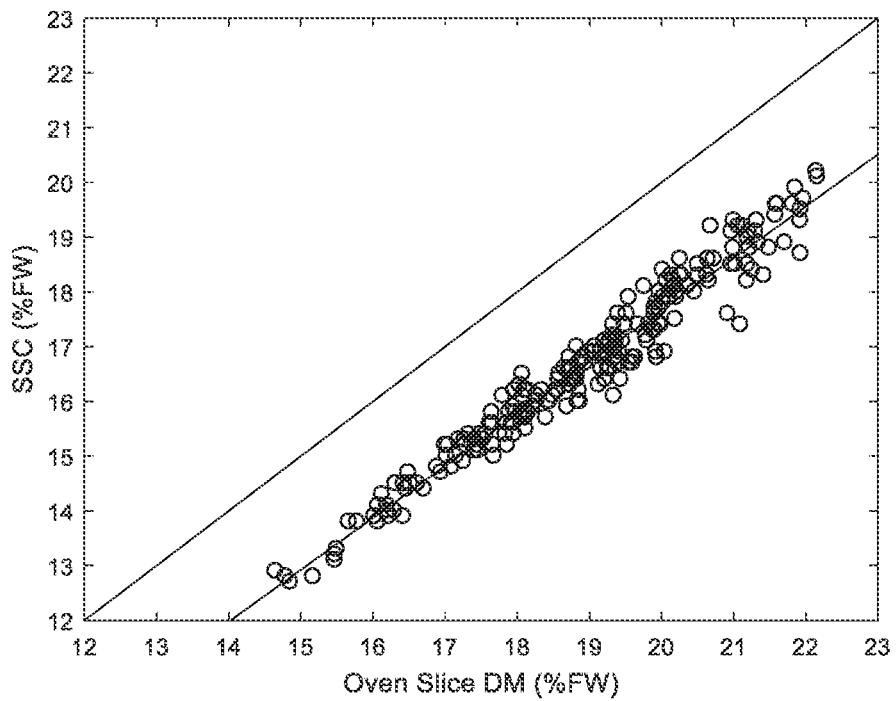
FIGS. 7A and 7B show that the method of the invention appears significantly better than slice DM (the current industry standard method) as a fruit quality indicator.
Figure 7B:
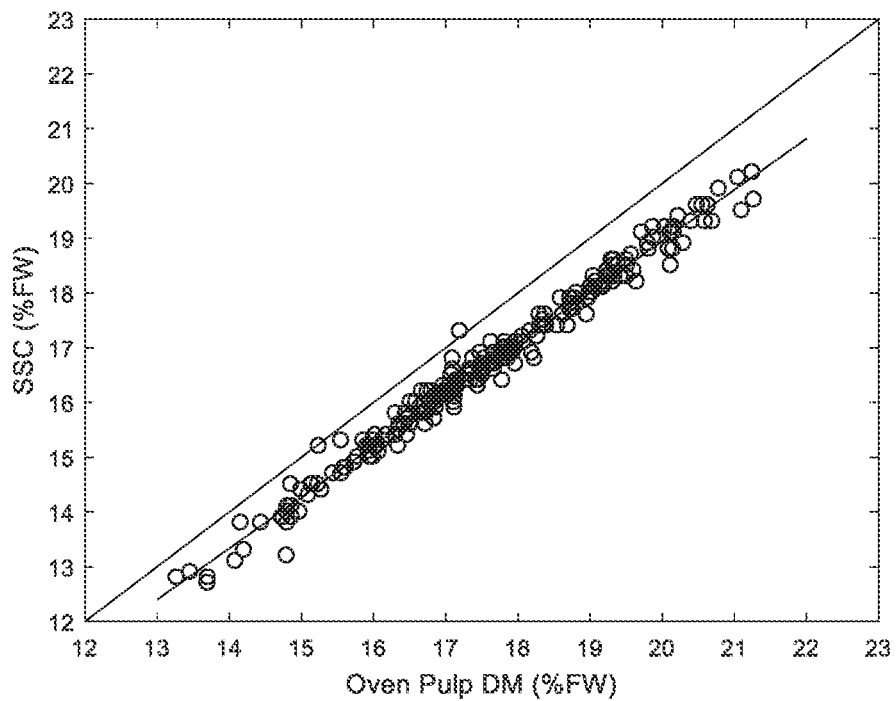
Figure 8:
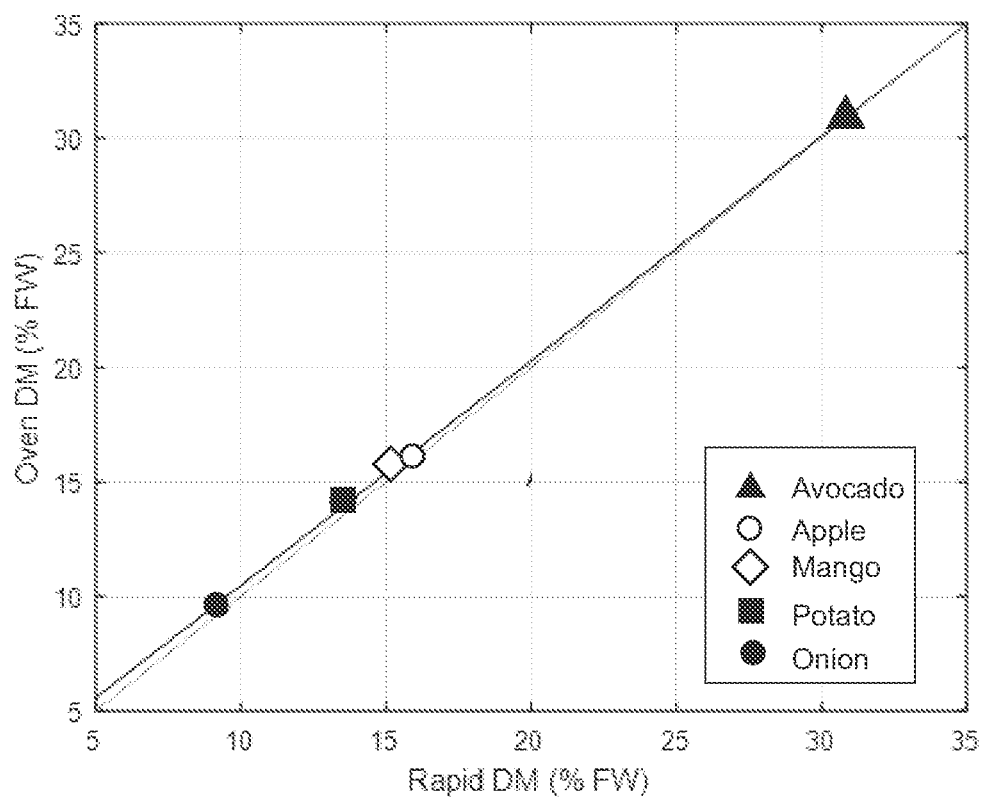
FIG. 8 shows the relationship between dry matter (DM) as estimated with the rapid pulp dry matter method of the invention, and dry matter (DM) as calculated with an industry standard Oven Pulp DM method.

The Rapid Pulp DM method of the invention appears significantly better than slice DM (the current industry standard method) as a fruit quality indicator, see FIGS. 7A and 7B. The final soluble solids content (SSC) of a ripe fruit is already known to be a primary indicator of kiwifruit consumer acceptability or taste quality. FIG. 7 shows there is less error or scatter around the regression line for the Rapid Pulp DM data.

Example 2

The method of the invention is exemplified below using apple, mango, potato, onion and avocado. Those skilled in the art will appreciate that the method can also be performed using other fruit and vegetables.

Summary

Apple (*Malus pumila*), mango (*Mangifera indica*), potato (*Solanum tuberosum*), onion (*Allum cepa*) and avocado (*Persea americana*) were evaluated for destructive analysis of dry-matter contents.

The rapid dry-matter measurement method of the invention was compared to the industry standard reference dry-matter measurements (involving 24 hours of drying) to assure that the rapid method of the invention is an accurate and feasible alternative to the industry standard methods.

Sample Preparation

Samples of each fruit or vegetable were prepared for use in the method of the invention and in the industry standard oven dry matter method involving 1 day of drying.

Each sample was cut up into approximately 5 mm sized pieces. These pieces were pulped according to the method described in Example 1 and approximately 20 g collected into sealed specimen containers prior to the drying procedure.

For both the rapid dry matter method and the reference method, four subsamples were taken from the pulps for testing.

Industry Standard (Conventional) Dry-Matter Method for Reference

For comparison, and to determine the accuracy of the rapid dry-matter method of the invention, industry standard methods for calculating dry matter were performed for each sample.

The pulped samples were thoroughly mixed just prior to sampling from the container.

The method was as follows:

1. Using a maker pen, the date, fruit sample number and pulp (if using more than one) were recorded on petri dishes.
2. The petri dishes were weighed on a scale with at least 3 decimal points and the weights ('dish wt') recorded.
3. The pulp (approximately 2-5 g) was placed onto the petri dishes then the weight ('dish+pulp wt') recorded again.
4. The petri dishes with the sample were placed in an oven set at 65° C. for 23.5 hours.
5. Once the incubation period had ended, the petri dishes were removed from the oven, allowed to cool for a few minutes, then the weight ('dry wt') recorded.

The dry matter content was calculated by using the following formula;

$$DM = \frac{100((\text{dish} + \text{dry wt}) - \text{dish wt})}{((\text{dish} + \text{wet wt}) - \text{dish wt})}$$

Rapid Dry-Matter Method of the Invention

The method for the rapid dry-matter experiment using glass fibre paper is as below. This method was followed for each sample.

1. Place a small, closed container (e.g., a plastic petri dish with lid) on the mass balance and zero the balance. This small, closed plastic container is used to contain the GF paper+pulp to prevent the pulp sample changing weight during the weighing process, which may take some seconds. Avoiding exposure to the environment during the weighing process helps to stabilise the weight of the pulp.
2. Weigh a piece of glass fibre (GF; Whatman Glass Microfibre Filters GF/A, 70 mm diameter, Cat No 1820-070) paper using a four decimal point weigh scale and record the weight. Use flat nose tweezers to handle the delicate glass fibre paper.
3. Place the GF paper on a small Teflon block, positioned so that the paper can be folded in half over the sample.
4. Mix the sample thoroughly by inversion and/or stirring.
5. Immediately after mixing, place about 0.3 g of pulp on the GF paper resting on the Teflon block using a small plastic pipette and the fold the GF paper over the pulp sample. Place another block on top and press firmly together without any rotation.
6. Place the GF paper+pulp (sandwich) sample inside the small plastic container, on the weight scale, and record the weight.
7. Switch on a pair of BOSCH-PHG 630 DCE, or similar, hot air guns to setting 3 at 150° C. The hot air gun will be secure in a retort stand set 4 cm away from the mesh. It is important to switch on the hot air gun prior to use as it takes time for the hot air gun to heat up to the required temperature.
8. Fasten each GF paper to the mesh between the two vertically opposed heat guns.
9. Heat the GF paper using the BOSCH-PHG 630 DCE, or similar, at setting 3, at 150° C. and with maximum flow rate. The heating time was 2.5 minutes from switching the guns on.
10. Place the GF paper and sample inside the small plastic container on the weight scales. Record the weight. The final weight reading happened quickly as the dried pulp will start to absorb moisture from the air which will affect the weight, hence the dry matter content.
11. The dry matter was calculated using the following formula:

$$\text{Dry matter \%} = 100 \frac{(\text{paper with dried sample} - \text{paper})}{(\text{paper with original sample} - \text{paper})}$$

Results

The calculated Rapid Pulp DM values were highly correlated with the values obtained using the Oven DM method (Table 1 and FIG. 7).

| Pulp Dry Matter (mean ± stdev; N = 4 reps) | | |
|---|---|---|
| | Rapid Pulp DM | Oven DM |
| Apple | 15.97 (±0.09) | 16.11 (±0.03) |
| Mango | 15.2 (±0.11) | 15.73 (±0.07) |
| Potato | 13.58 (±0.13) | 14.16 (±0.07) |
| Onion | 9.23 (±0.09) | 9.61 (±0.10) |
| Avocado | 30.87 (±0.07) | 30.93 (±0.09) |

The correlation with the Oven Pulp DM values was very high (R2=1), linear with slope close to 1, a small average bias (−0.34% FW) and a low root mean square error (rmse)=0.20% FW. Table 1 shows the dry matters of the tested fruit and vegetables for the method of the invention compared to oven drying at 65° C. The dry matters are expressed as % by weight of the pulp sample.

TABLE 1

| | DM Rapid | DM Oven pulp |
|---|---|---|
| apple | 15.9 | 16.2 |
| | 16.0 | 16.1 |
| | 15.9 | 16.1 |
| | 16.1 | 16.1 |
| mango | 15.2 | 15.7 |
| | 15.3 | 15.8 |
| | 15.1 | 15.7 |
| | 15.1 | 15.8 |
| potato | 13.7 | 14.2 |
| | 13.4 | 14.2 |
| | 13.5 | 14.2 |
| | 13.7 | 14.1 |
| onion | 9.1 | 9.7 |
| | 9.3 | 9.6 |
| | 9.3 | 9.5 |
| | 9.2 | 9.7 |
| avocado | 30.8 | 30.8 |
| | 30.9 | 30.9 |
| | 31.0 | 30.9 |
| | 30.8 | 31.0 |

Table 2 shows the average results for each type of fruit or vegetable tested. The average was calculated using 4 samples of each fruit or vegetable. Table 3 shows the standard deviations of results, again using 4 samples of each fruit or vegetable.

TABLE 2

| | DM Rapid | DM Oven Pulp |
|---|---|---|
| apple | 16.0 | 16.1 |
| mango | 15.2 | 15.7 |
| potato | 13.6 | 14.2 |
| onion | 9.2 | 9.6 |
| avocado | 30.9 | 30.9 |

TABLE 3

| | DM Rapid | DM Oven Pulp |
|---|---|---|
| apple | 0.09 | 0.03 |
| mango | 0.11 | 0.07 |
| potato | 0.13 | 0.07 |
| onion | 0.09 | 0.10 |
| avocado | 0.07 | 0.09 |

This again proves the Rapid Pulp DM method is very accurate for measuring expected Oven Pulp DM values.

Example 3

Summary

In an alternative embodiment, the material is homogenised directly on the support.

The method of the invention is exemplified below using kiwifruit. Those skilled in the art will appreciate that the method can also be performed using other fruit and vegetables.

Isolation of Outer Pericarp Material

A 10 mm equatorial slice (±1 mm) was cut from a Hayward kiwifruit (*Actinidia deliciosa*). A 7 mm inside-diameter cork-borer was used to take up to 8 plugs from the slice, between skin and seed-layer. Multiple plugs remained inside the borer to reduce premature moisture loss.

Rapid Dry-Matter Method of the Invention

Each sample was quickly placed in a pre-weighed cartridge comprising two layers of porous 60 gsm polypropylene "sample retainer" cloth (IndTex, Auckland, New Zealand) formed by heat-sealing the polypropylene into an 85×85 mm pocket, inside an aluminium-foil heat-sealable pouch (CasPak Ltd, Auckland, New Zealand). The purpose of the cartridge was to protect the sample against premature evaporation, sample loss on crushing and during drying, electrostatic effects during weighing, moisture regain between drying and weighing, and the buoyancy errors associated with weighing hot objects.

Figure 9:
FIG. 9 shows the cartridge support rolled up in an aluminium cylinder.

The cartridge was weighed by folding the cartridge loosely in two folds parallel to the open end (in thirds), and gently inserting it into the cartridge support on the balance. FIG. 9 shows the cartridge in an aluminium support. The weight of the cartridge was recorded.

The sample was crushed within the cartridge using a hydraulic press with a force of 4 tonnes borne by the sample. The fibrous component of the sample was reduced to a flake about 0.1 mm thick, and the rest of the sample was spread within the polypropylene pocket, to a diameter of about 60 mm.

The pocket, containing most of the sample, was removed from the pouch and placed on a pinpoint support midway between two opposed hot-air guns (Bosch PHG 630 DCE) 80 mm apart, set to 120° C. and level-2 air speed.

Figure 10:
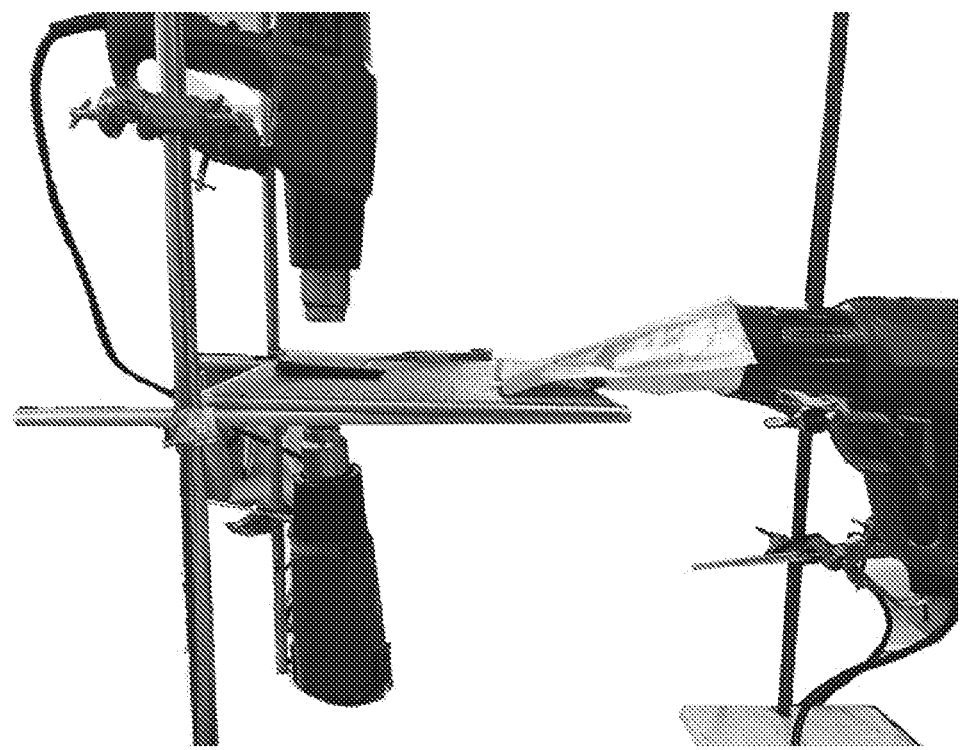
FIG. 10 shows the support structure for the three heat guns.

The emptied pouch, usually containing a small amount of liquid sample leaked from the cloth during crushing, was placed horizontally over the nozzle of a third hot-air gun set to 100° C. and level 2 air speed. The support structure used for the three heat guns is shown in FIG. 10.

The pocket and pouch were dried simultaneously for 8 minutes. Drying times of between 2 and 12 minutes were used in drying-completeness testing.

At the end of the drying period the pocket was promptly returned to the pouch, which was promptly heat sealed to prevent moisture uptake into the dried sample, and then fan-cooled for one minute to avoid buoyancy errors during weighing.

The pouch was then weighed on a 4-decimal-place recording balance to a stable reading.

The results were compared to a conventional oven drying method by taking a further seven adjacent plug samples from the same slice, drying them in open petri dishes in a 65° C. oven for 14 hours, and weighing and drying further for a total of 24 hours drying.

Results

Figure 11:
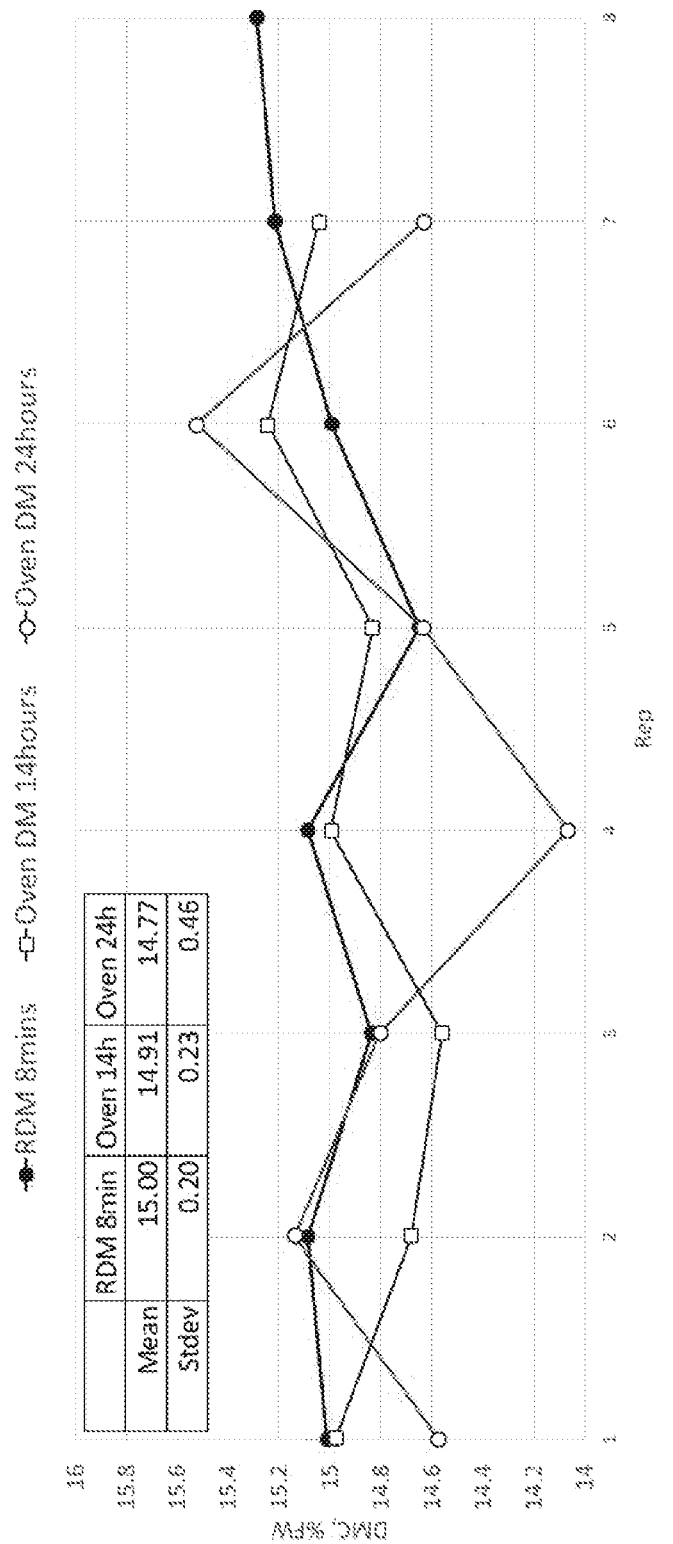
FIG. 11 shows the relationship between dry matter (DM) as estimated with the rapid pulp dry matter method of the invention, and dry matter (DM) as calculated with an industry standard Oven Pulp DM method.

The dry-matter content (DMC) results show that the 8-minute rapid drying method showed sample-to-sample variation with a standard deviation of 0.2% fresh weight units (% FW units). The oven-drying method, using samples from the same slice, showed a slightly larger variation. The mean DMC values from the rapid and oven methods were effectively the same, see FIG. 11.

Figure 12:
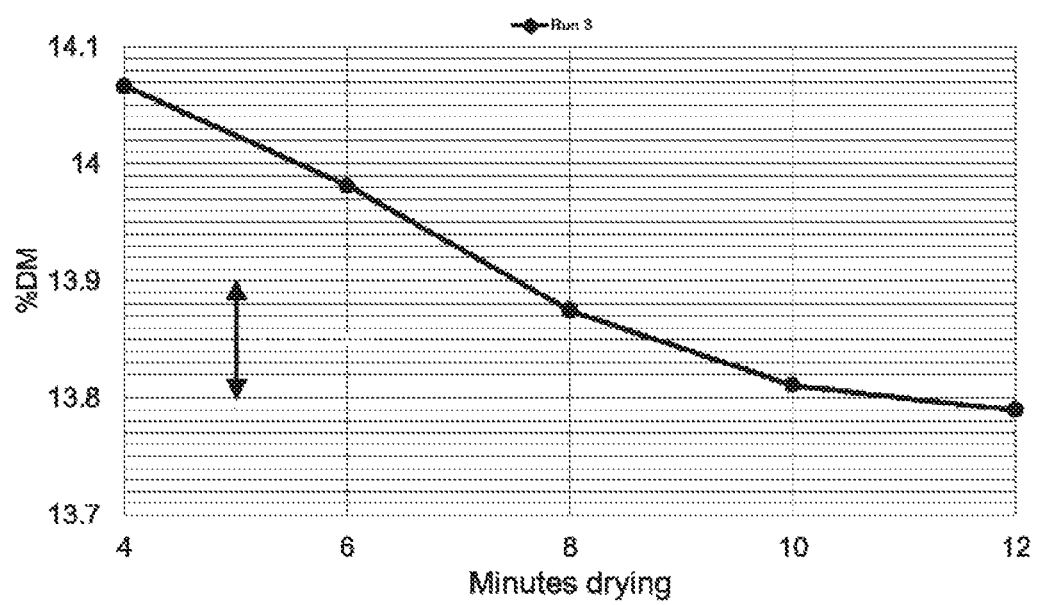
FIG. 12 shows the transformation of weight loss during drying into calculated percentage Dry-Matter.

The range of DMC value for the rapid method of the invention was from 14.6 to 15.2% FW. Considering the similar or greater range for the oven DMC figures, and the measurement deviation of less than 0.1% FW indicated in FIG. 12, it is likely that the variability within a single slice is real, perhaps related to small differences in proximity of the sampler to skin and seed regions, and the distribution of cell types within the fruit.

This again proves the Rapid Pulp DM method is very accurate for measuring expected Oven Pulp DM values.

We claim:

1. A method for estimating the dry matter content of a fruit or vegetable, the method comprising the steps
    a) providing material from the fruit or vegetable,
    b) homogenising the material,
    c) applying a portion of the homogenised material to a support,
    d) weighing the support and homogenised material,
    e) drying the homogenised material,
    f) weighing the support and dried homogenised material, and
    g) calculating dry matter content of the homogenised material based on the difference between the weight of the support and homogenised material and the weight of the support and dried homogenised material,
wherein the step of homogenising the material comprises forcing the material through an aperture at a force sufficient to break open cells in the material, and wherein the dry matter content of the homogenised material provides an estimate of the dry matter content of the fruit or vegetable.

2. The method according to claim 1, wherein the material is from the part of the fruit or vegetable that is consumed.

3. The method according to claim 1, wherein the fruit or vegetable is a fruit or vegetable for which dry matter content is used as indicator of quality.

4. The method according to claim 1, wherein the material comprises outer pericarp of a fruit and wherein the amount of any non-outer pericarp tissue amounts to less than 20% w/w of the material.

5. The method according to claim 1, wherein the aperture is no more than 1 mm in diameter.

6. The method according to claim 1, wherein the portion of homogenised material weighs no more than 10 g.

7. The method according to claim 1, wherein the support is or comprises at least one piece of absorbent material.

8. The method according to claim 7, wherein the support is or comprises at least two pieces of absorbent material.

9. The method according to claim 7, wherein the absorbent material is or comprises paper.

10. The method according to claim 9, wherein the paper is or comprises cellulosic paper, or is or comprises glass fibre paper.

11. The method according to claim 7, wherein the absorbent material is or comprises polypropylene or polyethylene.

12. The method according to claim 1, wherein the material is dispersed on the support to form a thin film and/or to increase the surface area of the material.

13. The method according claim 1, wherein the homogenised material is dried by the application of at least one of:
    a) heat, and
    b) air flow or turbulence.

14. The method according to claim 13, wherein the homogenised material is subjected to a temperature in the range 50 to 250° C.

15. The method according to claim 13, wherein the heat and/or air flow is applied to both sides of the support.

16. The method according to claim 3, wherein the fruit or vegetable is selected from the group consisting of kiwifruit, apples, pears, mangoes, melons, bananas, avocadoes, tomatoes, onions, potatoes, sweet potatoes and kumara.

* * * * *